United States Patent [19]

Hara et al.

[11] Patent Number: 4,939,667
[45] Date of Patent: Jul. 3, 1990

[54] SIGNAL PROCESSING METHOD FOR ANALYZING AUTORADIOGRAPH

[75] Inventors: Makoto Hara; Shu Sato, both of Minami-ashigara, Japan

[73] Assignee: Fuji Photo Film Co., Ltd., Kanagawa, Japan

[21] Appl. No.: 138,395

[22] Filed: Dec. 28, 1987

[30] Foreign Application Priority Data

Dec. 27, 1986 [JP] Japan .................................. 61-309754

[51] Int. Cl.$^5$ ...................... G06F 15/42; G01N 33/50
[52] U.S. Cl. ..................................... 364/497; 250/303; 364/413.01; 364/496; 435/6; 436/94; 935/77
[58] Field of Search .................... 364/413.01, 496, 497; 435/6; 250/303, 484.1 B, 327.2 A, 327.2 C, 327.2 D; 935/77; 436/94

[56] References Cited

U.S. PATENT DOCUMENTS

| | | | |
|---|---|---|---|
| 4,617,468 | 10/1986 | Shiraishi et al. | 250/327.2 A |
| 4,629,891 | 12/1986 | Nakajima et al. | 250/484.1 B |
| 4,665,312 | 5/1987 | Shiraishi et al. | 250/327.2 D |
| 4,706,192 | 11/1987 | Nasu et al. | 364/413.01 |
| 4,720,786 | 1/1988 | Hara | 364/413.01 |
| 4,734,581 | 3/1988 | Hashiue | 250/327.2 C |
| 4,748,326 | 5/1988 | Mori et al. | 250/484.1 B |
| 4,777,597 | 10/1988 | Shiraishi et al. | 364/413.01 |

Primary Examiner—Kevin J. Teska
Attorney, Agent, or Firm—Sixbey, Friedman, Leedom & Ferguson

[57] ABSTRACT

A signal processing method for analyzing an autoradiograph by subjecting digital image data containing an autoradiograph of a resolved pattern to digital signal processing to obtain locational information on radioactively labeled substances in the form of numerals and/or symbols is disclosed. The resolved pattern is formed by resolving radioactively labeled substances, such as, for example, nucleic acids, in a one-dimensional direction on a support medium. The total boundary area of the resolved patterns throughout the digital image data is determined by first dividing the digital image data into two or more blocks along a direction perpendicular to the resolving direction and then preparing a waveform composed of positions along the direction perpendicular to the resolving direction for each block by compiling the digital image date for each block. The waveform is used to establish the boundary of the area of the resolved pattern for each block, and the boundaries of the resolved pattern area of each block are interpolated to establish the total boundary area of the resolved patterns. This method is an easily conducted, accurate analytical method for obtaining locational information and, thus, the identity of a wide variety of radioactively labeled substances.

23 Claims, 3 Drawing Sheets

SIGNAL PROCESSING METHOD FOR ANALYZING AUTORADIOGRAPH

BACKGROUND OF THE INVENTION

1. Field of the Invention

This invention relates to a signal processing method for analyzing an autoradiograph.

2. Description of Prior Art

It is known that autoradiography can be used as a method for obtaining locational information on radioactively labeled substances distributed at least in one-dimensional direction on a support medium.

For instance, there is known an autoradiography method comprising steps of: labeling organism-originating biopolymers such as proteins and nucleic acids with a raidoactive element; resolving the mixture of the radioactively labeled biopolymers, derivatives thereof, cleavage products or synthetic products thereof on a gel support (medium) through a resolving process such as gel electrophoresis; placing the gel support medium and a high-sensitivity X-ray film together in layers for a certain period of time to expose said film to the gel support, and then performing the isolation and identification of the polymeric substances, determination of molecular weight of the polymeric substances and evaluation of characteristics of the polymeric substances based on the obtained locational information of the radioactively labeled substances from the exposed part of the film.

Recently, autoradiography has been effectively used especially for determining the base sequence of nucleic acids such as DNA and RNA. Further, autoradiography is an essential means for the screening of genes using a hybridization process such as Southern blotting, Northern blotting or colony hybridization.

For the purpose of simply carrying out the determinaion of the base sequence of nucleic acids with high accuracy in said autoradiography, there are described in co-pending U.S. patent application Ser. Nos.664,405 now abandoned and 837,037 (now abandoned) autoradiographic procedures which utilize a radiation image recording and reproducing method using a stimulable phosphor sheet in place of the above-mentioned conventional radiography using a radiosensitive material. The stimulable phosphor sheet comprises a stimulable phosphor and has such properties that when exposed to a radiation, the stimulable phosphor absorbs a portion of radiation energy and then emits light (stimulated emission) corresponding to the radiation energy stored therein upon excitation with an electromagnetic wave (stimulating rays) such as visible light or infrared rays. According to this method, exposure time can be greatly shortened and there is no trouble of causing problems such as chemical fog associated with prior arts. Further, since the autoradiograph having information on radioactively labeled substances is stored in the phosphor sheet as radiation energy and then read out as stimulated emission in time sequence, information can be expressed by the form of numerals and/or symbols in addition to an image.

The analysis of an autoradiograph has been conventionally made by visually judging each of resolved portions (bands) of the radioactively labeled substances on a visualized autoradiograph, thus obtaining locational information on the radioactively labeled specific substances (and identification of biopolymers, determination of molecular weight and evaluation of characteristics of biopolymers based on the obtained locational information of the radioactively labeled substances). For instance, the base sequence of the nucleic acids has been conventionally determined by visually comparing the positions of the bands of the mixture of the base-specific fragments of the nucleic acids such as DNA and RNA. Thus, the analysis of the autoradiograph requires great amounts of time and labor.

Further, since the visual analysis of the autoradiograph varies or fluctuates owing to the skill of investigators, the results on the determination of the base sequence of the nucleic acid vary depending on the investigators and the accuracy of information is limited to a certain extent.

In order to improve the accuracy of information, there are proposed in co-pending U.S. patent application Ser. Nos. 568,877 (now abandoned), 730,034, 91 and 917,609 methods for automatically obtaining locational information on the radioactively labeled substances in the form of numerals and/or symbols by obtaining the autoradiograph as digital signals and subjecting the digital signals to appropriate signal processing. The digital signals corresponding to the autoradiograph can be obtained either by visualizing the autoradiograph on a radiographic film and photoelectrically reading out the visible image on said film by means of reflected light or transmitted light when the conventional radiography is used, or by directly reading out the stimulable phosphor sheet without the visualization of the autoradiograph when the radiation image recording and reproducing method is used.

An autoradiograph of a pattern obtained on a support medium by electrophoretically resolving radioactively labeled substances contains various noises. Therefore, automatic analysis by digital signal processing is favorably employed. Even in the case that determination is performed on a visualized image, it is desired to subject the autoradiograph to gradation processing, enlargement processing and the like after converting the autoradiograph into digital image data.

Generally, the image data obtained from a radiation film or a radiation image storage panel contains image data of the overall surface of the film or panel. In other words, the image data contains not only digital image data of information on a resolved pattern but also digital data of extra area on the film or panel. Accordingly, in the case that signal processing is performed in the image processing for obtaining a visualized image or for automatic analysis, it is desired to first detect image data corresponding to a desired image area from the obtained digital image data and then perform the signal processing, so that quality and efficiency of the processing is enhanced.

SUMMARY OF THE INVENTION

The present inventor has invented an easily operated, accurate analytical method for autoradiography which comprises subjecting digital image data containing an autoradiograph of a resolved pattern to appropriate signal processing in the analysis of an autoradiograph having information on one-dimensional or two-dimensional location of radioactively labeled substances.

The present invention provides a signal processing method for analyzing an autoradiograph by subjecting digital image data containing an autoradiograph of a resolved pattern to digital signal processing to obtain information on the location of radioactively labeled substances in the form of numerals and/or symbols. The resolved pattern is formed by resolving radioactively labeled substances in one-dimensional direction on a support medium;

According to the present invention, digital image data is divided into two or more blocks along a direction perpendicular to the resolving direction for each block, and the digital image data for each block is added along the resolving direction to prepare a waveform composed of positions along the direction perpendicular to the resolving direction. The boundary area of the resolved pattern is detected from the waveform for each block, and the boundaries of the resolved pattern areas of the blocks are interpolated to determine a total boundary of the resolved patterns throughout the digital image data.

The present invention further provides a similar signal processing method for analyzing an autoradiograph which includes the additional step of detecting a boundary of each resolved row from the one-dimensional waveform for each block and then interpolating each of the boundaries of the resolved pattern areas and the boundaries of the resolved row of the blocks to determine the total boundary of each resolved row throughout the digital image data.

In the present invention, the term "locational information" of the radioactively labeled substances includes a variety of information relating to the location of the radioactively labeled substances, or the aggregation thereof, such as the position and shape of the aggregation of radioactive substances present in the sample, the concentration and distribution of the radioactive substances on the position, and combination thereof.

According to the invention, image data corresponding to a resolved pattern area can be selectively and accurately extracted (so called "draw out of image area") with ease from digital image data containing image information of an autoradiograph of both the resolved pattern and extra area. Moreover, if the resolved pattern contains plural patterns corresponding to plural resolved rows, the desired selective image data can be extracted for each resolved row.

The image data obtained in the invention precisely corresponds to data of the desired area even when the resolved pattern and resolved rows are curved or inclined to one side.

The image data appropriately extracted according to the invention can be subsequently subjected to the following autoradiographic process. Accordingly, image processing for obtaining a visual image suitable for visual analysis or signal processing for automatic analysis can be efficiently and accurately performed.

DETAILED DESCRIPTION OF THE INVENTION

Figure 1:
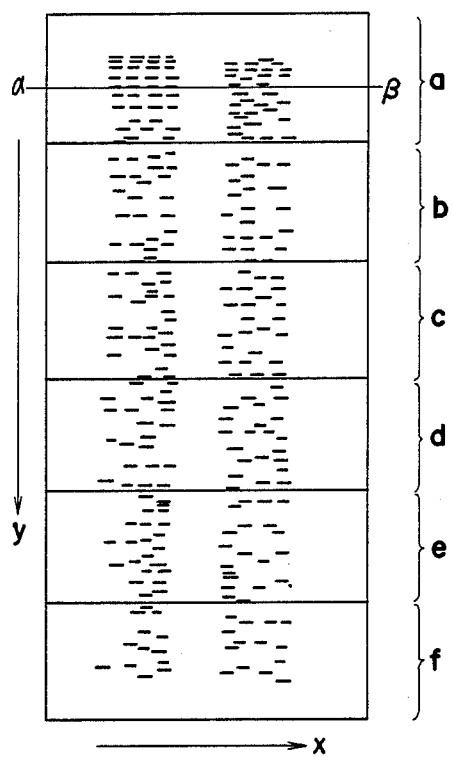
FIG. 1 is an example of an image prepared from digital image data containing an autoradiograph of a resolved pattern.

Examples of samples employable in the present invention include organism-originating biopolymers such as proteins, nucleic acids, derivatives thereof, cleavage fragments thereof and synthetic products thereof, which are labeled with a radioactive element.

Typical examples thereof are mixtures of base-specific fragments of nucleic acids such as DNA and RNA labeled with a radioactive element. The term "fragments" of nucleic acids means a plurality of different portions of a long-chain molecule. For instance, a mixture of base-specific DNA clevage products, which is a kind of a mixture of base-specific DNA fragments, can be obtained by base-specifically cleaving the radioactively labeled DNA according to the Maxam-Gilbert method. A mixture of base-specific DNA synthetic products can be obtained by synthesizing from raidoactively labeled deoxynucleoside triphosphates and DNA polymerase by the use of DNA as a template according to the Sanger-Coulson method. Mixtures of base-specific RNA fragments can be also obtained as a mixture of cleavage products or a mixture of synthetic products in a similar manner to the DNA method. DNA is composed of four kinds of bases: adenine, guanine, thymine and cytosine as its constitutional units, and RNA is composed of four kinds of bases: adenine, guanine, uracil and cytosine.

These substances can be labeled with a radioactive element such as $^{32}P$, $^{14}C$, $^{35}S$, $^{3}H$ or $^{125}I$ by any of appropriate methods.

A sample, which is a mixture of the base-specific fragments of a nucleic acid labeled with a radioactive element, can be resolved (developed) on a known support medium such as a gel support medium by any of conventional resolving (developing) procedures such as electrophoresis, thin layer chromatography, column chromatography and paper chromatography.

The support medium on which the radioactively labeled substances are resolved, is autoradiographed by means of the conventional radiography using a radiosensitive material or the radiation image recording and reproducing method using a stimulable phosphor sheet. The digital image data containing the autoradiograph of the radioactively labeled substance are then obtained through an appropriate read-out system.

When the conventional radiography is used, the support medium and a radiosensitive material such as an X-ray film are placed together in layers at a low temperature or at room temperature for a long period of time (several hours to several tens of hours) to give exposure to the radiographic film. The radiographic film is then developed to visualize the autoradiograph of the radioactively labeled substances on the film, and the visualized autoradiograph is read out using an image read-out system. For instance, the radiographic film is irradiated with an optical beam and a beam transmitted or reflected is photoelectrically detected, whereby the visualized autoradiograph can be transformed into electric signals. Further, the electric signals are converted into digital image data through A/D conversion.

When the radiation image recording and reproducing method is used, the support medium and the stimulable phosphor sheet are placed together in layers at an ambient temperature for a short period of time (several seconds to several tens of minute) to store radiation energy radiating from the radioactively labeled substances in the phosphor sheet, whereby the autoradiograph is recorded as a kind of a latent image (energy-stored image) on the phosphor sheet. The stimulable phosphor sheet, for example, has a basic structure where a support such as a plastic film, a phosphor layer comprising a stimulable phosphor such as a divalent europium activated barium fluorobromide phoshpor (BaFBr:Eu$^{2+}$) and transparent protective film are laminated in order. The stimulable phosphor has characteristics of absorbing and storing radiation energy when irradiated with a radiation such as X-rays and subsequently releasing the stored radiation energy as stimulated emission when excited with visible light to infrared rays.

Then, the autoradiograph stored and recorded on the stimulable phosphor sheet is read out using a read-out system. For instance, the phosphor sheet is scanned with a laser beam to release the radiation energy stored in the stimulable phosphor as light emission and the emitted light is photoelectrically detected, so that the autoradiograph can be directly obtained as electric signals without visualization thereof. Further, the electric signals are converted into digital image data containing the autoradiograph through A/D conversion. The above-described methods for measuring the autoradiograph and obtaining the digital image data containing the autoradiograph are described in more detail in the aforementioned U.S. patent application Ser. Nos. 568,877 (now abandoned) and 837,037 (now abandoned).

While the methods for obtaining the digital image data containing the autoradiograph of the radioactively labeled substances resolved on a support meduim using the conventional radiography and the radiation image recording and reproducing method are described above, the present invention is not limited thereto and digital image data obtained by any other method can be applied to the signal processing method of the invention, provided that they contain the autoradiograph.

The obtained digital image data are a set of digital signals $D_{xy}$ defined by coordinates (x,y) which are represented by a coordinate system fixed to the radiographic film or the stimulable phosphor sheet and signal level (z) at the coordinate. The signal level represents the density of image at the coordinate, that is, the amount of the radioactively labeled substances. Accordingly, the digital image data have information on two-dimensional location of the radioactively labeled substances.

The thus-obtained digital image data containing the autoradiograph of the radioactively labeled substances resolved on a support meduim is subjected to signal processing to analyze the autoradiograph according to the present inventioon described in more detail below.

The signal processing method of the present invention will be described by referring to an example of an electrophoretic pattern of electrophoretic rows (resolved rows) which are formed by resolving (developing) a sample on a support medium by electrophoresis, said sample being composed of a combination of the following four groups of base-specific DNA fragments labeled with a radioactive element:

(1) guanine (G) - specific DNA fragments,
(2) adenine (A) - specific DNA fragments,
(3) thymine (T) - specific DNA fragments,
(4) cytosine (C) - specific DNA fragments, Each group of the base-specific DNA fragment is composed of DNA fragments which are synthesized according to the Sanger-Coulson method and have various lengths and the same base at terminals.

The digital image data containing the autoradiograph of the base-specific DNA fragments are stored temporarily in a memory device of a signal processing circuit (that is, stored in a nonvolatile memory unit such as a buffer memory, a magnetic disk, etc.).

FIG. 1 shows an example of an autoradiographic image visualized directly from the resulting digital image data, and contains two resolved patterns. Each resolved pattern comprises four lanes corresponding respectively to the above-mentioned four samples.

First, the digital image data containing image information of FIG. 1 are divided into two or more blocks along a direction perpendicular to the resolving direction. The term "resolving direction" is intended not to mean an actual electrophoretically resolving direction in the strict sense, but to mean an intended resolution direction, that is, the major axis direction (y-direction) of the support meduim (that is, a radiographic film or a stimulable phosphor sheet).

The number of the blocks obtained by dividing the image data varies depending on the type of the sample, the number of the bands, the amount of the data and the change of signal level (density gradient), but is preferably 5 to 6.

When the image data are divided into plural blocks along a direction (x-direction) perpendicular to the resolving direction and subjected to the following operational processing, the draw-out of the pattern as well as the draw-out of the lane can be accurately performed even if the resolved pattern and lanes are curved or inclined to one side.

In FIG. 1, the image data are divided into six blocks of (a) to (f).

Second, the image data are added along the y-direction for each block to prepare a one-dimensional waveform composed of positions in the x-direction and signal level in the positions.

Figure 2:
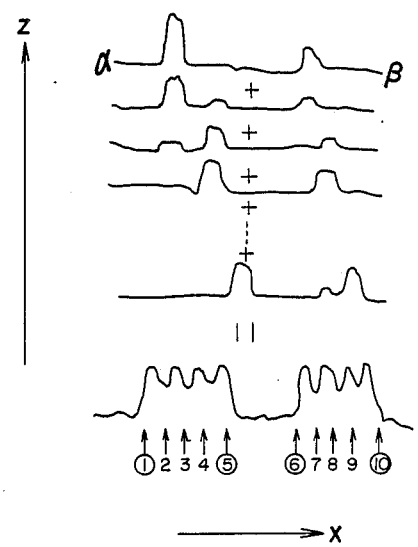
FIG. 2 shows schematically a procedure for obtaining projection of one block.

FIG. 2 indicates schematcially a procedure for the preparation of the one-dimensional waveform.

For instance, if the image data are extracted along the α-β line in the (a) block of FIG. 1, a one-dimensional waveform composed of positions in the x-direction and their signal levels (z) is prepared as shown at the top of FIG. 2. The prepared one-dimensional waveform represents a sectional view along the α-β line. All of the image data contained in the (a) block are extracted to prepare similar one-dimensional waveforms, which are then added along the y-direction to give an accumlatted one-dimensional waveform (i.e., projection) shown at the bottom of FIG. 2.

Since combinations of four base-specific DNA fragments are exclusive of each other, each one-dimensional (sectional image) contains sectional images of a portion of 8 lanes such as sectional images of one or two lanes. However, the accumlated one-dimensional waveform (projection) clearly contains sectional views of all 8 lanes.

The addition of image data can be performed by adding signals corresponding to all pixels (i.e., image unit) as described above. Alternatively, signals corresponding to a portion of the pixels can be added for simplifying the addition operation. If all image data are added in the case that approx. 2,000 pixels are arranged in the y-direction, 300 to 400 pixels are added in the y-direction after division into 5 to 6 blocks. The portional additional of image data can be performed by extracting signals along the y-direction at equal intervals and adding the extracted signal. In this method, only 10 to 50% of the whole image data can be subjected to the addition operation.

In advance of obtaining the projection by addition of image data, each one-dimensional waveform ($\alpha$-$\beta$ of FIG. 2) can be subjected to appropriate operations such as if differential operation. For instance, differential operation is applied, the edge of each sectional image is represented in the form of peaks of plus or minus. Therefore, an improved clear image can be produced.

Third, a boundary of the resolved pattern area is detected on the basis of the obtained one-dimensional waveform (projection).

The boundary of the resolved pattern area can be detected, for instance, by obtaining an average of signal levels (z) of the one-dimensional waveform, obtaining a threshold value ($z_a$) by multiply the average an appropriate number, and then obtaining a point on which the one-dimensional waveform crosses the threshold value.

Figure 3:
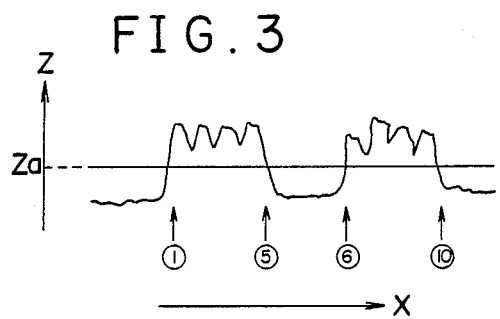
FIG. 3 shows examples of respective boundaries of one-dimensional waveform and resolved pattern area.

FIG. 3 indicates a one-dimensional waveform and examples of boundaries of a resolved pattern area which are detected on the one-dimensional waveform.

In FIG. 3, arrows ($\uparrow$) 1, 5, 6 and 10 indicate respective boundaries of the resolved pattern area. In more detail, the area sandwiched between the arrows 1 and 5, and the are a sandwiched between the arrows 6 and 10 both are the resolved pattern area.

Fourth, a boundary of each lane is detected on the basis of the one-dimensional waveform (projection).

Since the resolved pattern area is already obtained, a boundary of the lane can be detected by obtaining a point on which the signal level reaches a minimum value within the resolved pattern. The minimum point can be determined by detecting a point on which the sign of difference inverses.

Figure 4:
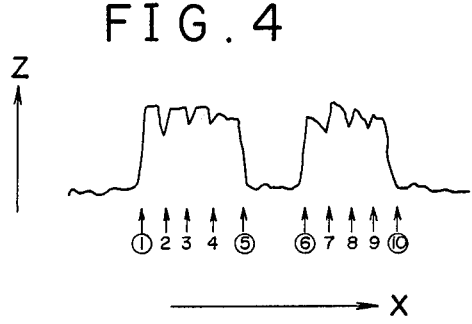
FIG. 4 shows examples of respective boundaries of one-dimensional waveform and lanes.

FIG. 4 indicates a one-dimensional waveform and examples of boundaries of a lane detected on the waveform.

In FIG. 4, arrows ($\uparrow$) 2, 3, 4, 7, 8 and 9 represent respective boundaries of the lane detected in the above operation. In more detail, boundaries of four lanes of the resolved pattern on the left side are represented by arrows 1-5, and boundaries of four lanes of the resolved pattern on the right side are represented by arrows 6-10.

Thus, boundaries of two resolved pattern areas and boundaries of eight lanes in the block (a) are all detected. In a similar manner, boundaries of the resolved pattern area and boundaries of the lanes in the remaining blocks (b) to (f) can be detected.

If the differential operation is performed prior to obtaining the projection as described above, boundaries of each lane can be detected by alternately finding peaks on the plus side and peaks on the minus side.

Fifth, the boundaries of the resolved pattern area and the boundaries of the lanes detected in respective blocks are interpolated to determine an overall boundary of the pattern area and an overall boundary of the lanes.

Figure 5:
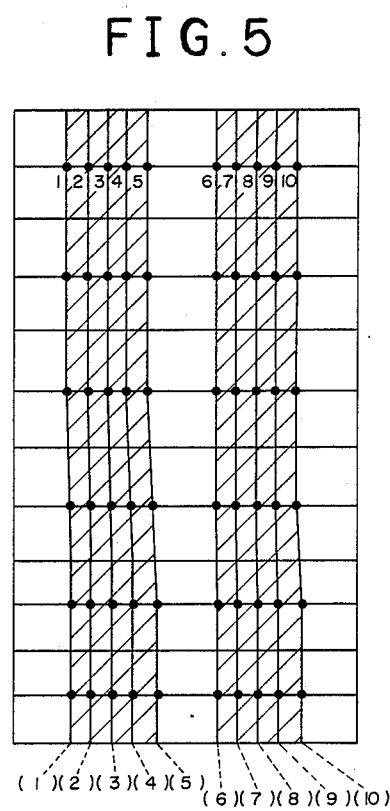
FIG. 5 shows schematically a procedure for obtaining boundaries of a resolved pattern and a whole lane respectively.

For instance, the boundary points of the resolved pattern area and lanes represented by arrows 1 to 10 in FIG. 4 are fixed on a center line which is arranged along the x-direction and divides the block (a) into two area as shown in FIG. 5.

FIG. 5 schematically illustrates examples of operations for determining boundaries of the resolved pattern and the whole lanes.

Figure 6:
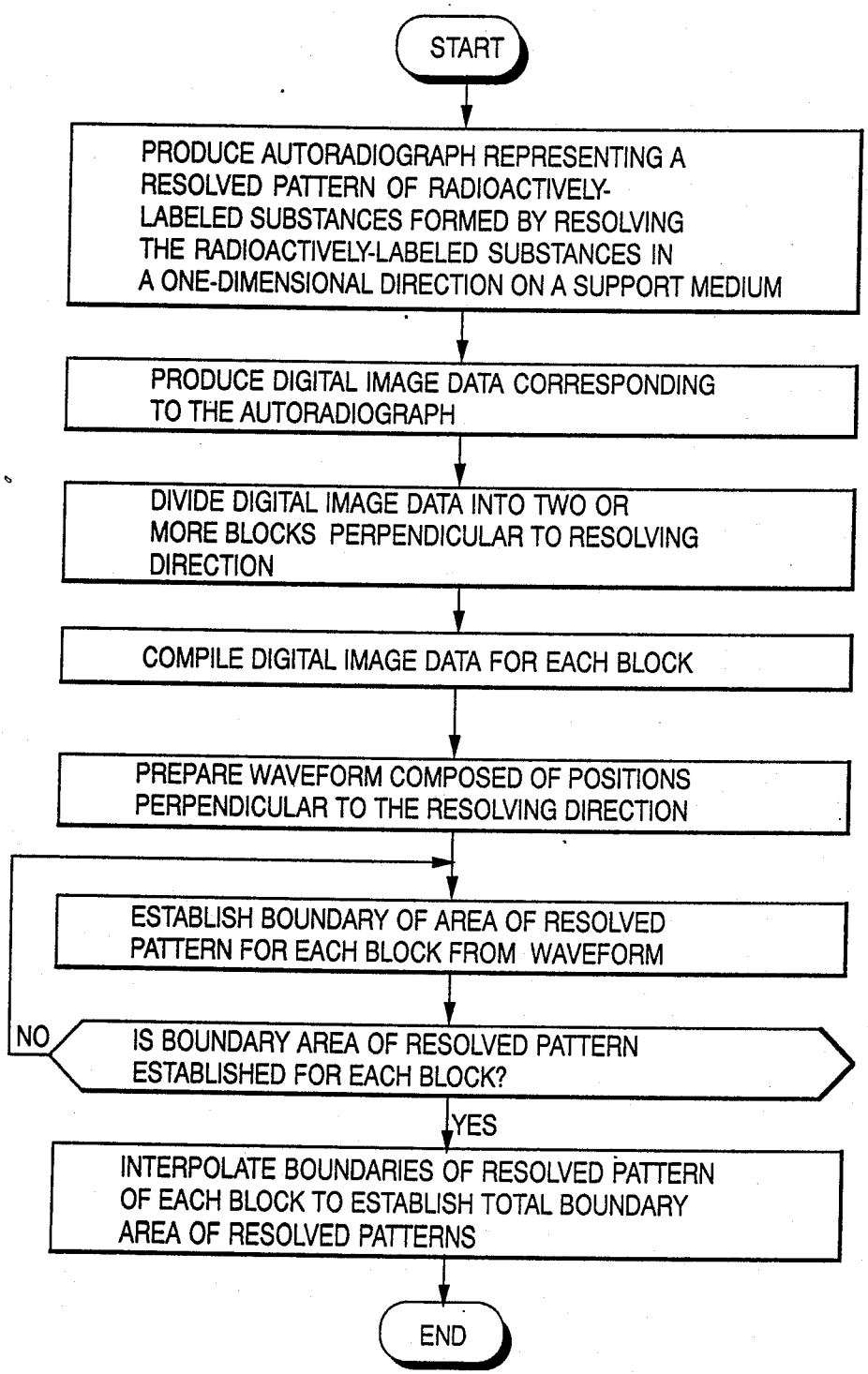
FIG. 6 is a flowchart representing the process of the present invention.

FIG. 6 illustrates a flowchart which represents one embodiment of the present digital signal processing method for automatically analyzing an autoradiograph.

In similar manners, respective boundary points are detected on center lines in the remaining blocks, and the detected boundary points corresponding to each other are connected in sequence to prepare boundary lines (1) and (5) as well as (6) and (10) for two resolved patterns, and boundary lines of (1), (2), (3), (4) and (5) as well as (6), (7), (8), (9) and (10) for eight lanes.

For instance, if it is intended to draw out only the resolved patterns, the image data corresponding to the area sandwiched between the boundary lines (1) and (5) and the boundary lines (6) and (10) are extracted. If it is intended to draw out each lane, for example, the left side lane on the left side pattern, the image data sandwiched between the boundary lines (1) and (2) are extracted.

The digital image data containing an autoradiograph of a resolved pattern can be processed not only to draw out the data along the width direction (x-direction) but also to draw out the data along the longitudinal direction (y-direction). For instance, an image area along the longitudinal direction only can be drawn out by applying a similar operation along the longitudinal direction. The operation applicable to the longitudinal direction can be more simplified, because the resolved pattern has less fluctuation in the longitudinal direction.

The digital image data corresponding to the resolved pattern area and each lane which are determined by the aforementioned signal processing are output from the signal processing circuit and transmitted to other signal processing circuits directly or via a recording means such as a magnetic disc or a magnetic tape.

The digital image data obtained to correspond to the image area can be further subjected efficiently to known image processings such as gradation processing, spatial frequency processing, enlargement processing, compaction processing, and addition/average processing. By applying these known processing to the digital image data, an image which is improved in image quality and is more appropriate for submitting to analysis can be obtained.

If the autoradiograph is automatically analyzed by a signal processing, an appropriate signal processing can be applied to each of a resolved pattern and a lane after subjecting the image data corresponding to the resolved pattern or lane. Accordingly, processing efficiency is improved, and further accuracy of locational information such as informaiton for base sequencing is enhanced.

In the above-described example, there has been described the case containing two resolved patterns and eight lanes, but the present invention is by no means limited thereto, and the method of the present invention can also be applied to the cases where one or more than two resolved patterns are involved. Further, one resolved pattern may contain one or more lanes. Furthermore, in the case that a plurality of lanes are involved, the present invention is by no means limited to the mixture of base-specific DNC fragments which are exclusive of each other, and other combination can be used. The sample of the present invention is not limited to the base-specific DNA fragments. The method of the present invention can be applied to various resolved patterns of radioactively labeled substances resolved in one-dimensional direction on a support medium by various resolving means. Particularly, the method of the present invention is suitable for use in carrying out the microanalysis of proteins as well as the screening of genes.

We claim:

1. A signal processing method for analyzing an autoradiograph to obtain locational information on radioactively labeled substances in a one-dimensional resolving direction on a support meduim, wherein the signal processing method subjects to digital signal processing digital image data containing an autoradiograph obtained by placing the support meduim and a stimulable phosphor sheet comprising a stimulable phosphor together in layers to record the autoradiograph of radioactively labeled substances on the support meduim on said phosphor sheet, irradiating said phosphor sheet with stimulating rays and photoelectrically detecting the autoradiograph as stimulated emission, wherein the autoradiograph is analyzed by:

(a) dividing the digital image data into two or more blocks along a direction perpendicular to the resolving direction;

(b) preparing a waveform composed of positions along the direction perpendicular to the resolving direction for each block by compiling the digital image data for each block;

(c) using the waveform to establish a boundary of an area of a resolved pattern for each block; and (d) interpolating the boundaries of the resolved pattern area of each block to establish a total boundary area to the resolved patterns.

2. The signal processing method as claimed in claim 1, wherein all of the digital image data are compiled along the resolving direction in step b.

3. The signal processing method as claimed in claim 1, wherein the digital image data are extracted along the resolving direction at equal spaces and the extracted data are compiled in step (b).

4. The signal processing method as claimed in claim 1, wherein a mean signal level of the waveform is determined, a threshold value is determined on the basis of the mean signal level, and a point corresponding to the threshold value on the waveform is assigned to the boundary of the pattern area established in step (c).

5. The signal processing method as claimed in claim 1, wherein the boundary of the resolved pattern area is determined on a central line along the direction perpendicular to the resolving direction for each block and boundary points of the blocks which correspond to each other are connected in sequence to determine the total boundary throughout the resolved pattern areas established in step (d).

6. The signal processing method as claimed in claim 1, wherein said radioactive labeled substances are nucleic acids, derivatives thereof, cleavage products thereof or synthetic products thereof labeled with a radioactive element, and locational information obtained by signal processing is information on the base sequence thereof.

7. A signal processing method for analyzing an autoradiograph to obtain locational information on radioactively labeled substance in a one-dimensional resolving direction on a support medium, wherein the signal processing method subjects to digital signal processing digital image data containing an auto-radiograph obtained by placing said support medium and a radiographic film together in layers to record the autoradiograph of radioactively labeled substances on said support medium on said radiographic film as a visible image and photoelectrically reading out the autoradiograph visualized on said radiographic film, wherein the autoradiograph is analyzed by:

(a) dividing the digital image data into two or more blocks along a direction perpendicular to the resolving direction;

(b) preparing a waveform composed of positions along the direction perpendicular to the resolving direction for each block by compiling the digital image data for each block;

(c) using the waveform the establish a boundary of an area of a resolved pattern for each block; and (d) interpolating the boundaries of the resolved pattern area of each block to establish a total boundary are of the resolved patterns.

8. The signal processing method as claimed in claim 7, wherein all of the digital image data are compiled along the resolving direction in step (b).

9. The signal processing method as claimed in claim 7, wherein the digital image data are extracted along the resolving direction at equal spaces and the extracted data are compiled in step (b).

10. The signal processing method as claimed in claim 7, wherein a mean signal level of the waveform is determined, a threshold value is determined on the basis of the mean signal level, and a point corresponding to the threshold value on the waveform is assigned to the boundary of the pattern area established in step (c).

11. The signal processing method as claimed in claim 7, wherein the boundary of the resolved pattern area is determined on a central line along the direction perpendicular to the resolving direction for each block and boundary points of the blocks which correspond to each other are connected in sequence to determine the total boundary throughout the resolved pattern areas established in step (d).

12. A signal processing method for analyzing an autoradiograph to obtain locational information on radioactively labeled substances represented on said autoradiograph by a resolved pattern including a plurality of resolved rows formed by resolving the radioactively labeled substances in a one-dimensional resolving direction on a support meduim, wherein the signal processing method subjects to digital signal processing digital image data containing an autoradiograph obtained by placing the support meduim and a stimulable phosphor sheet together in layers to record the autoradiograph of radioactively labeled substances on the support meduim on said phosphor sheet, irradiating said phosphor sheet with stimulating rays and photoelectrically detecting the autoradiograph as stimulated emission, wherein the autoradiograph is analyzed by:

(a) dividing the digital image data into two or more blocks along a direction perpendicular to the resolving direction;

(b) preparing a waveform composed of positions along the direction perpendicular to the resolving direction for each block by compiling the digital image data for each block;

(c) using the waveform to establish a boundary of an area of the resolved pattern for each block;

(d) using the waveform to establish a boundary of each resolved row in each block; and (e) interpolating the boundaries of each of the resolved pattern areas and the boundaries of the resolved rows of each block to establish a total boundary of each resolved row.

13. The signal processing method as claimed in claim 12, wherein all of the digital image data are compiled along the resolving direction in step b.

14. The signal processing method as claimed in claim 12, wherein the digital image data are extracted along the resolving direction at equal spaces and the extracted data are compiled in step (b).

15. The signal processing method as claimed in claim 12, wherein a mean signal level of the waveform is determined, a threshold value is determined on the basis of the mean signal level, and a point corresponding to the threshold value on the waveform is assigned to the boundary of the pattern area established in step (c).

16. The signal processing method as claimed in claim 12, wherein a point at which is the signal level is made minimum of the waveform in the pattern area is assigned to the boundary of a resolved row established in step (d).

17. The signal processing method as claimed in claim 12, wherein the boundary of the resolved pattern area and the boundary of the resolved row are determined on a central line along the direction perpendicular to the resolving direction for each block and boundary points of the blocks which correspond to each other are connected in sequence to determine the total boundary throughout the resolved rows established in step (e).

18. A signal processing method for analyzing an autoradiograph to obtain locational information on radioactively labeled substances represented on said autoradiograph by a resolved pattern including a plurality of resolved rows formed by resolving the radioactively labeled substances in a one-dimensional resolving direction on a support medium, wherein the signal processing method subjects to digital signal processing digital image data containing an autoradiograph obtained by placing said support meduim and a radiographic film together in layers to record the autoradiograph of radioactively labeled substances on said support meduim on said radiographic film as a visible image and photoelectrically reading out the autoradiograph visualized on said radiographic film, wherein the autoradiograph is analyzed by:

(a) dividing the digital image data into two or more blocks along a direction perpendicular to the resolving direction;

(b) preparing a waveform composed of positionl along the direction perpendicular to the resolving direction for each block by compiling the digital image data for each block;

(c) using the waveform to establish a boundary of an area of the resolved pattern for each block;

(d) using the waveform to establish a boundary of each resolved row in each block; and (e) interpolating the boundaries of each of the resolved pattern areas and boundaries of the resolved rows of each block to establish a total boundary of each resolved row.

19. The signal processing method as claimed in claim 18, wherein all of the digital image data are compiled along the resolving direction in step b.

20. The signal processing method as claimed in claim 18, wherein the digital image data are extracted along the resolving direction at equal spaces and the extracted data are compiled in step (b).

21. The signal processing method as claimed in claim 18, wherein a mean signal level of the waveform is determined, a threshold value is determined on the basis of the mean signal level, and a point corresponding to the threshold value on the waveform is assigned to the boundary of the pattern area established in step (c).

22. The signal processing method as claimed in claim 18, wherein a point at which the signal level is made minimum on the waveform in the pattern area is assigned to the boundary of a resolved row established in step (d).

23. The signal processing method as claimed in claim 18, wherein the boundary of the resolved pattern area and the boundary of the resolved row are determined on a central line along the direction perpendicular to the resolving direction for each block and boundary points of the blocks which correspond to each other are connected in sequence to determine the total boundary throughout the resolved rows established in step (e).

* * * * *